(12) United States Patent
Fedosya et al.

(10) Patent No.: US 8,268,938 B2
(45) Date of Patent: Sep. 18, 2012

(54) MALEIMIDE BASED COMPOUND, COMPOSITION FOR FORMING BOARD, AND BOARD FABRICATED USING THE SAME

(75) Inventors: Kalinina Fedosya, Ulan-Ude (RU); Myung-Sup Jung, Seongnam-si (KR); Chung-Kun Cho, Suwon-si (KR); Jae-Jun Lee, Suwon-si (KR); Kwang-Hee Kim, Seoul (KR)

(73) Assignees: Samsung Electronics Co., Ltd. (KR); Samsung Fine Chemicals Co., Ltd. (KR); Samsung Electro-Mechanics Co., Ltd. (KR)

( * ) Notice: Subject to any disclaimer, the term of this patent is extended or adjusted under 35 U.S.C. 154(b) by 250 days.

(21) Appl. No.: 12/542,460

(22) Filed: Aug. 17, 2009

(65) Prior Publication Data

US 2010/0215973 A1 Aug. 26, 2010

(30) Foreign Application Priority Data

Feb. 26, 2009 (KR) .................. 10-2009-0016502

(51) Int. Cl.
*C08L 67/00* (2006.01)
*C08L 77/00* (2006.01)
(52) U.S. Cl. ........ 525/445; 525/418; 525/420; 525/426; 525/437
(58) Field of Classification Search .................. 525/418, 525/420, 426, 437, 445
See application file for complete search history.

(56) References Cited

U.S. PATENT DOCUMENTS

| 5,227,429 A * | 7/1993 | Kawamura et al. .......... 525/92 J |
| 5,789,757 A * | 8/1998 | Husson et al. ........... 252/183.11 |
| 2010/0022716 A1* | 1/2010 | Pan et al. ...................... 525/375 |

FOREIGN PATENT DOCUMENTS

| FR | 2206317 | 11/1972 |
| KR | 10-1992-0009888 A | 6/1992 |

\* cited by examiner

*Primary Examiner* — Ana Woodward
(74) *Attorney, Agent, or Firm* — Cantor Colburn LLP

(57) ABSTRACT

Disclosed is a composition for forming a board. The composition includes a maleimide-based compound including at least three maleimide groups and a liquid crystalline polymer or oligomer. A prepreg and a board are each fabricated using the composition.

9 Claims, 4 Drawing Sheets

MALEIMIDE BASED COMPOUND, COMPOSITION FOR FORMING BOARD, AND BOARD FABRICATED USING THE SAME

CROSS-REFERENCE TO RELATED APPLICATION

This application claims priority to Korean Patent Application No. 10-2009-0016502, filed on Feb. 26, 2009, and all the benefits accruing therefrom under 35 U.S.C. 119, the content of which in its entirety is herein incorporated by reference.

BACKGROUND (a) Field

A maleimide-based compound, a composition including the maleimide-based compound for forming a board, and a board fabricated using the same are provided.

(b) Description of the Related Art

Electronic devices such as computers, semiconductor devices, displays, and communication devices typically include printed electronic circuit boards, also referred to herein simply as "boards". A printed electronic circuit board may include a wire for transferring signals (also referred to as "signal lines"), an insulation layer or layers for preventing a short circuit between wires, a switching element, and other elements.

A printed electronic circuit may be formed into a thin film to provide increased performance in some electronic devices, and may also be formed to have a very small size to allow the printed electronic circuit to fit into a small package, such as in handheld devices (e.g., cell phones, personal digital assistants, and the like). In this way, various performance factors compatible with the needs of the consumer and packaging and performance requirements should be taken into consideration in the design of a printed electronic circuit board.

SUMMARY

In an embodiment, a composition is provided for forming a board having improved surface characteristics and heat resistance.

In another embodiment, a composition for forming a board is provided, which has improved solubility.

Also in an embodiment, a composition for forming a board includes a maleimide-based compound having at least three maleimide groups and a liquid crystalline polymer or oligomer.

The maleimide-based compound includes compounds represented by the following Chemical Formula 1 or 2, or a combination comprising at least one of the foregoing.

Chemical Formula 1

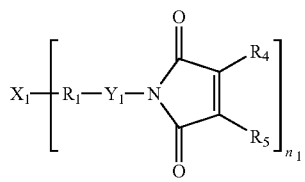

Chemical Formula 2

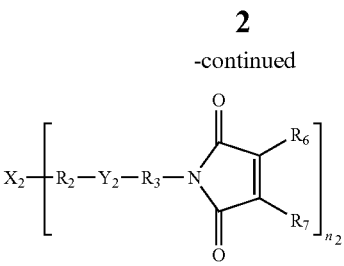

In the above Chemical Formulae 1 and 2, $R_1$ to $R_3$ are independently a substituted or unsubstituted C6 to C24 arylene, $R_4$ to $R_7$ are independently hydrogen or a C1 to C5 alkyl, $Y_1$ and $Y_2$ are independently $C(=O)O$, $C(=O)NH$, O, CO, or a combination comprising at least one of the foregoing, and $n_1$ and $n_2$ are independently integers from 3 to 6, provided that when $n_1$ is 3, $X_1$ is CR, $P(=O)$, SiR, SiOR, or a combination comprising at least one of the foregoing, where R is hydrogen or a C1 to C5 alkyl; when $n_1$ is 4, $X_1$ is C, Si, or SiO; and when $n_1$ is 5, $X_1$ is P, and when $n_2$ is 3, $X_2$ is CR, $P(=O)$, SiR, SiOR, or a combination comprising at least one of the foregoing, where R is hydrogen or a C1 to C5 alkyl; when $n_2$ is 4, $X_2$ is C, Si, SiO, or a combination comprising at least one of the foregoing; and when $n_2$ is 5, $X_2$ is P.

The maleimide-based compound may include compounds represented by the following Chemical Formulae 3 to 6, or combinations comprising at least one of the foregoing.

Chemical Formula 3

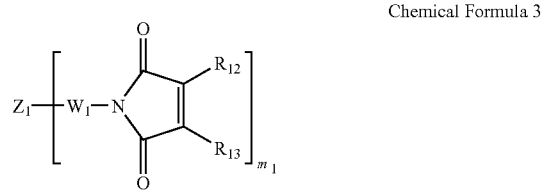

Chemical Formula 4

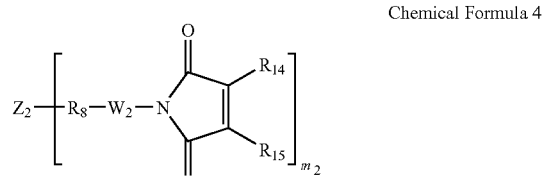

Chemical Formula 5

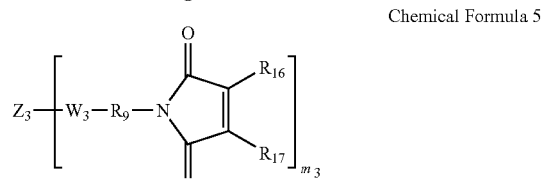

Chemical Formula 6

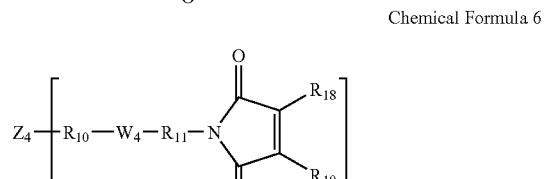

In the above Chemical Formulae 3 to 6, $R_8$ to $R_9$ are independently a substituted or unsubstituted C6 to C24 arylene, $R_{12}$ to $R_{19}$ are independently hydrogen or a C1 to C5 alkyl, $W_1$ to $W_4$ are independently $C(=O)O$, $C(=O)NH$, O, or a combination comprising at least one of the foregoing, $m_1$ to $m_4$ are independently integers from 3 to 8, and $Z_1$ to $Z_4$ are independently a substituted or unsubstituted C3 to C10 cycloalkylene, a substituted or unsubstituted C6 to C24 arylene, or a combination comprising at least one of the foregoing.

The liquid crystalline polymer or oligomer may include at least one of C(=O)O, O, C(=O)NR', NR', CO, a substituted or unsubstituted C6 to C30 aromatic cyclic group, or a combination comprising at least one of the foregoing, in its main chain, and where R' is hydrogen or a C1 to C5 alkyl.

The liquid crystalline polymer or oligomer may include an end group of hydroxy, a maleimide group, a nadimide group, a phthalimide group, an acetylene group, a propargyl ether group, a benzocyclobutene, a cyanate, a substituted or unsubstituted alicyclic group including a double bond or a triple bond, an alkenyl or alkynyl group including an aryl substituent, or a combination comprising at least one of the foregoing, at the terminus of the liquid crystalline polymer or oligomer.

In another embodiment, a maleimide-based compound represented by one of the above Chemical Formulae 1 to 6 is provided.

In another embodiment, a prepreg fabricated from the composition for forming a board is provided.

In another embodiment, a board that is fabricated from the composition for forming a board is provided.

Hereinafter, further embodiments will be described in detail.

DETAILED DESCRIPTION

Figure 1:
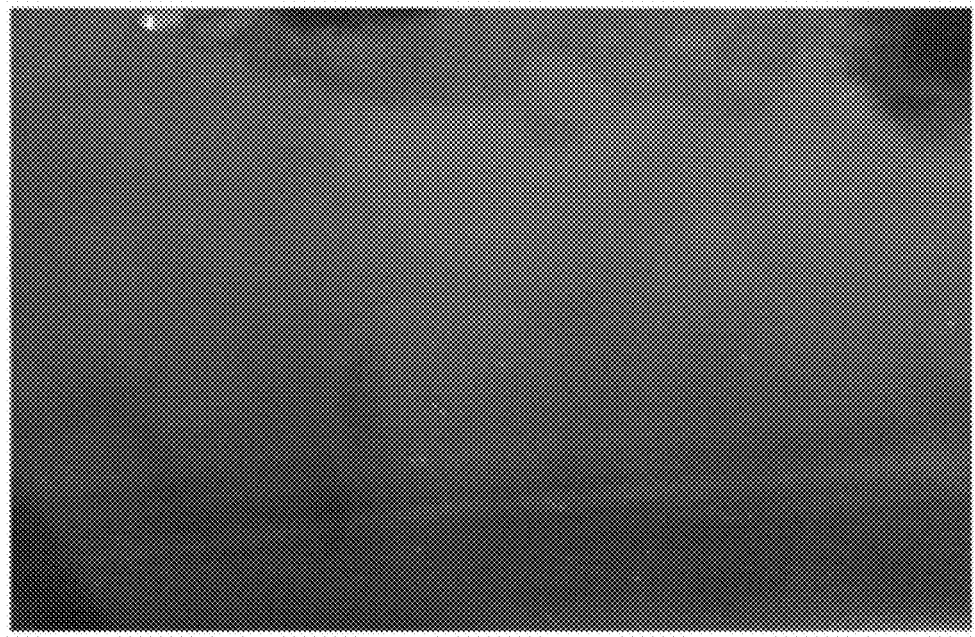
FIG. 1 is a scanning electron micrograph ("SEM") image showing the surface of an exemplary prepreg according to Example 1.

Exemplary embodiments of the present invention will hereinafter be described in detail. However, these embodiments are only exemplary, and the present invention is not limited thereto. In this regard, the present embodiments may have different forms and should not be construed as being limited to the descriptions set forth herein. Accordingly, the embodiments are merely described below, by referring to the figures, to explain aspects of the present description.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, regions, integers, steps, operations, elements, and/or components, but do not preclude the presence or addition of one or more other features, regions, integers, steps, operations, elements, components, and/or groups thereof. All ranges and endpoints reciting the same feature are independently combinable.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Also as used herein, when specific definition is not provided, the term "substituted" refers to one substituted with at least a substituent selected from a halogen; a C1 to C20 alkyl such as for example methyl, ethyl, n-propyl, isopropyl, n-butyl, isobutyl, t-butyl, n-pentyl, and the like; a C1 to C20 alkoxy such as for example methoxy, ethoxy, n-propoxy, isopropoxy, n-butoxy, isobutoxy, t-butoxy, n-pentoxy, and the like, a C6 to C30 aryl such as for example phenyl, biphenyl, tolyl, methoxyphenyl, trifluoromethylphenyl, naphthyl, anthracyl, fluorenyl, and the like; or a C6 to C30 aryloxy such as for example phenyloxy, biphenyloxy, tolyloxy, methoxyphenyloxy, trifluoromethylphenyloxy, naphthyloxy, anthracyloxy, fluorenyloxy, and the like, or a combination comprising at least one of the foregoing.

As used herein, when a specific definition is not provided, the terms "an alkenyl", "an alkynyl", and "an aryl" respectively refer to a C2 to C20 alkenyl such as for example ethenyl, propenyl, 1- or 2-butenyl, isobutenyl, 1-, 2-, or 3-pentyl, and the like, a C2 to C20 alkynyl such as for example ethynyl, n-propyl, isopropyl, n-butyl, isobutyl, t-butyl, n-pentyl, and the like, and a C6 to C30 aryl.

Also as used herein, "prepreg" is a sheet comprising uncured or partially cured composition for forming a board, which does not have a metal layer laminated to it. A prepreg may be reinforced with, for example, glass fiber, polymer fibers, and the like, which may be in the form of a woven or nonwoven mat. Also as used herein, a board includes a prepreg having one or more layers of a metal cladding, such as for example copper, laminated to a surface of the prepreg.

The composition for forming a board according to one embodiment includes a maleimide-based compound including at least three maleimide groups and a liquid crystalline polymer or oligomer. Exemplary components included in the composition for forming a board will hereinafter be described in detail.

Maleimide-Based Compound

The maleimide-based compound includes at least three maleimide groups which may be identical or different. In an embodiment, the maleimide groups are each bonded to a central group by tethering groups which may be identical or different.

The maleimide-based compound includes compounds represented by the following Chemical Formula 1 or 2, or a combination comprising at least one of the foregoing.

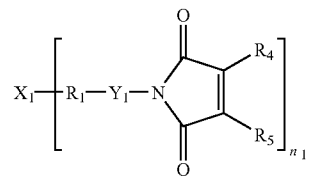

Chemical Formula 1

-continued

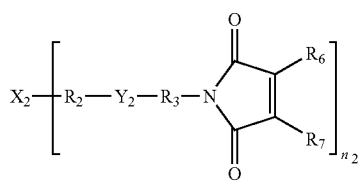

Chemical Formula 2

In the above Chemical Formulae 1 and 2, $R_1$ to $R_3$ are independently a substituted or unsubstituted C6 to C24 arylene, $R_4$ and to $R_7$ are independently hydrogen or a C1 to C5 alkyl, $Y_1$ and $Y_2$ are independently $C(=O)O$, $C(=O)NH$, O, CO, or a combination comprising at least one of the foregoing, and $n_1$ and $n_2$ are independently integers from 3 to 6, provided that when $n_1$ is 3, $X_1$ is CR, $P(=O)$, SiR, SiOR, or a combination comprising at least one of the foregoing, where R is hydrogen or a C1 to C5 alkyl; when $n_1$ is 4, $X_1$ is C, Si, or SiO; and when $n_1$ is 5, $X_1$ is P, and when $n_2$ is 3, $X_2$ is CR, $P(=O)$, SiR, or SiOR where R is hydrogen or a C1 to C5 alkyl; when $n_2$ is 4, $X_2$ is C, Si, or SiO; and when $n_2$ is 5, $X_2$ is P.

The maleimide-based compound may include compounds represented by the following Chemical Formulae 3 to 6, or combinations comprising at least one of the foregoing.

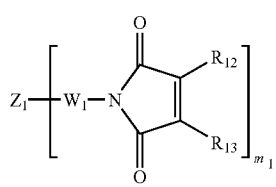

Chemical Formula 3

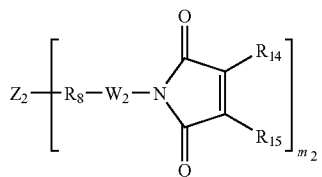

Chemical Formula 4

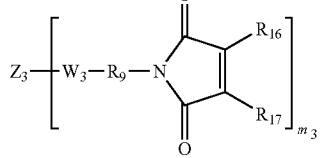

Chemical Formula 5

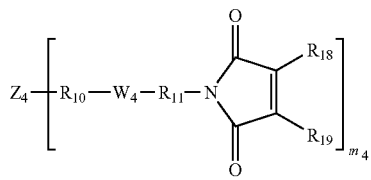

Chemical Formula 6

In the above Chemical Formulae 3 to 6, $R_8$ to $R_9$ are independently a substituted or unsubstituted C6 to C24 arylene, $R_{12}$ to $R_{19}$ are independently hydrogen or a C1 to C5 alkyl, $W_1$ to $W_4$ are independently $C(=O)O$, $C(=O)NH$, O, or a combination comprising at least one of the foregoing, $m_1$ to $m_4$ are independently integers from 3 to 8, and $Z_1$ to $Z_4$ are independently a substituted or unsubstituted C3 to C10 cycloalkylene, a substituted or unsubstituted C6 to C24 arylene, or a combination comprising at least one of the foregoing. As used herein, exemplary C3 to C10 cycloalkylene groups include cyclopropylene, cyclobutylene, cyclopentylene, cyclohexylene, cycloheptylene, cyclooctylene, bis(cyclohexylene), 1,4-cyclohexydimethylene, disubstituted decalins, and the like. Also as used herein, exemplary C6 to C24 arylenes include phenylene, biphenylene, naphthalene, anthracenylene, fluorenylene, and the like.

The weight ratio of a liquid crystalline polymer or oligomer and a maleimide-based compound, for the composition for forming a board may be, respectively, about 1:9 to about 9:1, and in a more specific embodiment, about 2:8 to about 8:2. In addition, when the liquid crystalline polymer or oligomer and the maleimide-based compound are present in these proportions, desirable properties such as the mechanical characteristics, physiochemical characteristics, and other desirable characteristics of the board formed from the composition may be further improved. Furthermore, when the maleimide-based compound is added at in a greater amount relative to the liquid crystalline polymer or oligomer, the thermal expansion coefficient of a board prepared therefrom may be reduced.

Liquid Crystalline Polymer or Oligomer

The liquid crystalline polymer or oligomer includes an aromatic cyclic group in its main chain. Where a liquid crystalline oligomer is used, the oligomer may have a number average molecular weight (Mn) from about 500 to about 10,000. Where a liquid crystalline polymer is used, the polymer may have a number average molecular weight (Mn) from about 10,000 to about 1,000,000.

The liquid crystalline polymer or oligomer may include at least one of $C(=O)O$, O, $C(=O)NR'$, NR', CO, a substituted or unsubstituted C6 to C30 aromatic cyclic group, or a combination comprising at least one of the foregoing in its main chain, and where R' is hydrogen or a C1 to C5 alkyl. The aromatic cyclic group has a cyclic structure in which functionality, such as the unsaturated bonds and the lone pairs, are randomly distributed, which means a functional group in which the electrons are delocalized or resonated. For example, the aromatic cyclic group includes an aryl group, a heteroaryl group in which at least one of CH present in a ring of the aryl group is substituted with a hetero atom such as N, O, S, and P, an oxyheteroaryl group, and the like, and a combination comprising at least one of the foregoing. The liquid crystalline polymer or oligomer includes at least two aromatic cyclic groups that are different from each other in the main chain.

In an embodiment, the aromatic cyclic group is at least one selected from the group consisting of the following Chemical Formulae 7-1 to 7-5. In addition, it may be at least one selected from the group consisting of the following Chemical Formulae 7-1 to 7-5 and at least one selected from the group consisting of the following Chemical Formulae 8-1 to 8-5. In addition, in the following Chemical Formulae 7-1 to 7-5 and the following Chemical Formulae 8-1 to 8-5, at least one of the halogen atom or C1 to C5 alkyl group of the benzene ring may be substituted.

The functional group represented by the following Chemical Formulae 7-1 to 7-5 may be included in an amount of about 5 mol % to about 60 mol % based on the total moles of monomer in the liquid crystalline polymer or oligomer. When present in this amount, the solubility in solvent is further improved and the viscosity of the composition can be adjusted.

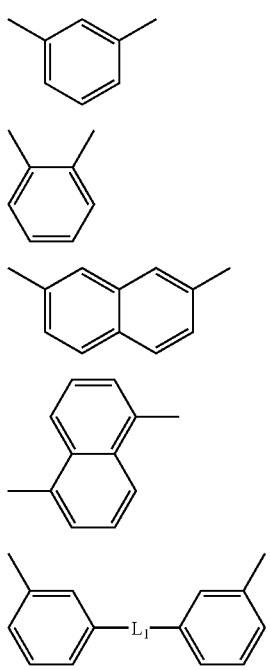

Chemical Formula 7-1

Chemical Formula 7-2

Chemical Formula 7-3

Chemical Formula 7-4

Chemical Formula 7-5

In the above Chemical Formula 7-5, $L_1$ is a divalent organic functional group, such as.

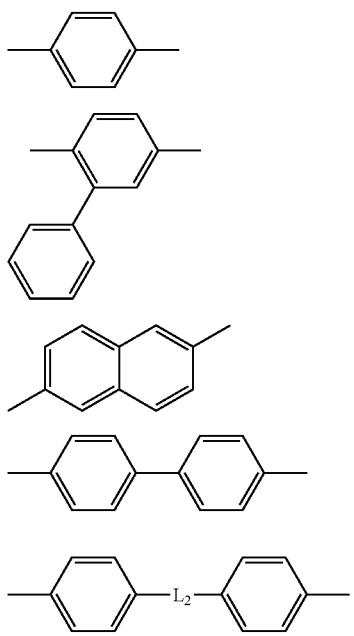

Chemical Formula 8-1

Chemical Formula 8-2

Chemical Formula 8-3

Chemical Formula 8-4

Chemical Formula 8-5

In the above Chemical Formula 8-5, $L_2$ is a divalent organic functional group.

In the above Chemical Formulae 7-5 and 8-5, $L_1$ and $L_2$ may be represented by one or more of the following Chemical Formulae 9-1 to 9-11. Furthermore, the benzene ring in these structures may be substituted with at least one of a halogen atom, a C1 to C5 alkyl group, and the like in the following Chemical Formulae 9-1 to 9-11.

—O—  
Chemical Formula 9-1

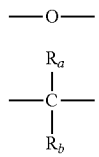

Chemical Formula 9-2

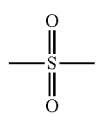

Chemical Formula 9-3

—N=N—  
Chemical Formula 9-4

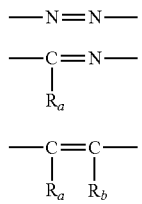

Chemical Formula 9-5

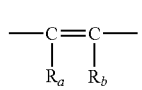

Chemical Formula 9-6

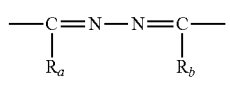

Chemical Formula 9-7

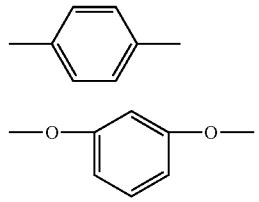

Chemical Formula 9-8

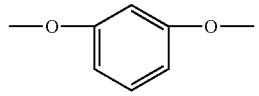

Chemical Formula 9-9

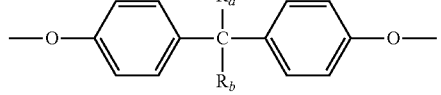

Chemical Formula 9-10

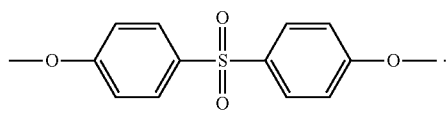

Chemical Formula 9-11

In the above Chemical Formulae 9-1 to 9-11, $R_a$ and $R_b$ are independently hydrogen, a halogen, a C1 to C5 alkyl, or a combination comprising at least one of the foregoing.

The liquid crystalline oligomer may be represented by the following Chemical Formula 10-1.

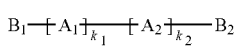

Chemical Formula 10-1

In the above Chemical Formula 10-1, $A_1$ is represented by the following Chemical Formula 10-2, $A_2$ is represented by the following Chemical Formula 10-3, $B_1$ and $B_2$ are thermally curable cross-linking reactive groups including a multiple bond at the terminal end, and $k_1$ and $k_2$ are independently integers from 1 to 50.

—$Y_3$—$Ar_1$—$Y_4$—      Chemical Formula 10-2

In the above Chemical Formula 10-2, $Y_3$ and $Y_4$ are independently C(=O)O, O, C(=O)NR, NR, CO, or a combination comprising at least one of the foregoing, where R is hydrogen, a C1 to C20 alkyl, a C6 to C30 aryl, or a combination comprising at least one of the foregoing, and Ar₁ is one selected from the group consisting of the above Chemical Formulae 7-1 to 7-5 and combinations thereof.

   Chemical Formula 10-3

In the above Chemical Formula 10-3, $Y_5$ and $Y_6$ are independently C(=O)O, O, C(=O)NR, NR, CO, or a combination comprising at least one of the foregoing, where R is hydrogen, a C1 to C20 alkyl, or a C6 to C30 aryl, and Ar₂ is one selected from the group consisting of the above Chemical Formulae 8-1 to 8-5 and combinations thereof.

In the above Chemical Formula 10-1, the quotient $k_1/(k_1+k_2+2)$ is greater than about 0.5 to less than or equal to about 0.6.

The liquid crystalline polymer or oligomer may include an end group including a hydroxy group, a maleimide group, a nadimide group, a phthalimide group, an acetylene group, a propargyl ether group, a benzocyclobutene group, a cyanate group, a substituted or unsubstituted alicyclic group including a double bond or a triple bond, an alkenyl or alkynyl including an aryl substituent, or a combination comprising at least one of the foregoing at its terminus.

The alicyclic group may include a C3 to C30 cycloalkyl group, a C3 to C30 cycloalkynyl group, a C3 to C30 cycloalkenyl group, a C3 to C30 heterocycloalkyl group (where at least one of $CH_2$, CH, and C of the ring of the cycloalkyl group is substituted with N, O, S, P, or a combination comprising at least one of the foregoing), a C3 to C30 heterocycloalkynyl group, a C3 to C30 heterocycloalkenyl group, and the like. Thus, in the heterocycloalkyl group, the heterocycloalkynyl group, and the heterocycloalkenyl group, at least one of $CH_2$, CH, and C of a ring(s) of the cycloalkyl group, the cycloalkynyl group, and the cycloalkenyl group is substituted with N, O, S, P, or a combination comprising at least one of the foregoing.

For example, the liquid crystalline polymer or oligomer may include as end groups a functional group selected from the group consisting of the following Chemical Formulae 11-1 to 11-6 and combinations thereof at the terminus.

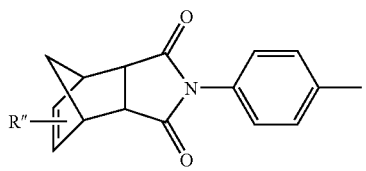   Chemical Formula 11-1

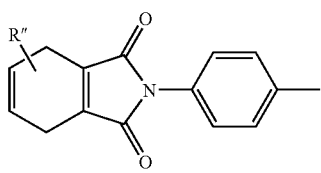   Chemical Formula 11-2

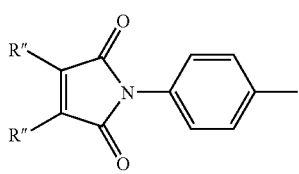   Chemical Formula 11-3

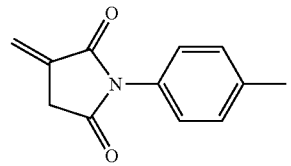   Chemical Formula 11-4

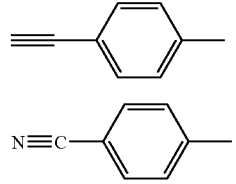   Chemical Formula 11-5

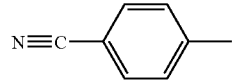   Chemical Formula 11-6

In the above Chemical Formulae 11-1 to 11-6, R" is hydrogen, a substituted or unsubstituted C1 to C20 alkyl, a substituted or unsubstituted C6 to C30 aryl, or a combination comprising at least one of the foregoing.

The composition for forming a board may further include a solvent. The composition for forming a board has improved solubility in a solvent and more consistently maintains the viscosity. In an embodiment, the solvent may be a polar aprotic solvent. Non-limiting examples of the solvent may include N,N-dimethyl acetamide, N-methylpyrrolidone ("NMP"), N-methylcaprolactam, N,N-dimethyl formamide ("DMF"), N,N-diethylformamide, N,N-diethylacetamide, N-methyl propionamide, dimethylsulfoxide ("DMSO"), γ-butyrolactone, dimethylimidazolidinone, tetramethylphosphoric amide, ethylcellulose acetate, a combination comprising at least one of the foregoing, and the like. In an embodiment, the solvent may be included to provide a solids content for the composition of about 5 to about 95 percent solids, specifically about 10 to about 90 percent solids, and more specifically about 30 to about 50 percent solids, based on the total weight of liquid crystal polymer or oligomer, maleimide-based compound, any additives and/or fillers, and solvent.

The composition for forming a board may include about 5 to about 95 parts by weight of the liquid crystalline polymer or oligomer and about 5 to about 95 parts by weight of a bismaleimide-based cross-linking agent, based on the liquid crystalline polymer or oligomer and the bismaleimide-based cross-linking agent.

The composition for forming a board may further include a polymer such as a thermally curable resin, a thermoplastic resin, an oligomer thereof, a combination comprising at least one of the foregoing, provided that the desired characteristics and properties of the composition for forming a board are not significantly adversely affected. For example, the composition for forming a board may further include a phosphorous compound such as phosphoric acid ester or phosphoric acid melamine, a nitrogen-included compound such as melamine or benzoguanamine, an oxazine cycle-containing compound, a silicon compound, a polyimide, a polyvinylacetal, a phenoxy resin, an acrylic resin, an acrylic resin which includes a hydroxy or carboxyl group, an alkyd resin, elastomers such as, for example, a polyurethane resin, polybutadiene, a butadiene-acrylonitrile copolymer, polychloroprene, a butadiene-styrene copolymer, polyisoprene, a butyl rubber, a fluoro rubber, a natural rubber, a styrene-isoprene rubber, an acrylic rubber, an epoxylated butadiene, or a maleated butadiene, polyethylene, polypropylene, a polyethylene-propylene copolymer, polyvinyl chloride, polyvinylidene chloride, polystyrene, polyvinyl toluene, polyvinyl phenol, an acrylonitrile styrene resin, an acrylonitrile butadiene styrene resin, a (meth)acrylate-butadiene-styrene resin, poly-4-fluoroethylene, fluoroethylene-propylene, 4-fluoroethylene-6-fluoroethylene, vinylidene fluoride, polycarbonate, polyester carbonate, polyphenylene ether, polysulfone, polyester, polyether sulfone, polyamide, polyamide imide, polyester imide, polyphenylene sulfite, a (meth)acrylate, an epoxy(meth)acrylate, di(meth)acryloxy-bisphenol, poly(meth)acrylate, styrene, vinylpyrrolidone, diacryl phthalate, divinylbenzene, diallylbenzene, diallyl ether bisphenol, trialkenyl isocyanurate, dicyclopentadiene, a phenolic resin, polymers, oligomers or resins which include a monomer having a polymerizable double bond such as an unsaturated polyester or prepolymers thereof, a curable monomer such as polyisocyanate or prepolymers thereof, a combination comprising at least one of the foregoing, and the like.

The composition for forming a board may further include fillers, softening agents, plasticizers, antioxidants, flame retardants, flame-retardant aids, lubricants, anti-static agents, colorants, heat stabilizers, light stabilizers, UV absorbers, a combination comprising at least one of the foregoing, and the like.

The filler may include organic fillers and/or inorganic fillers. Non-limiting examples of the organic fillers include epoxy resin powder, melamine resin powder, urea resin powder, benzoguanamine resin powder, a styrene resin, a combination comprising at least one of the foregoing, and on the like. Non-limiting examples of the inorganic fillers include natural silica, fused silica, amorphous silica, hollow silica, aluminum hydroxide, boehmite, magnesium hydroxide, molybdenum oxide, zinc molybdate, zinc borate, zinc stannate, aluminum borate, potassium titanate, magnesium sulfate, silicon carbide, zinc oxide, silicon nitride, silicon dioxide, aluminum titanate, barium titanate, barium strontium titanate, aluminum oxide, alumina, clay, kaolin, talc, calcined clay, calcined kaolin, calcined talc, mica, short glass fiber, a combination comprising at least one of the foregoing, and the like. Fillers, including both organic and inorganic fillers, may be used alone or as a mixture of two or more.

Non-limiting examples of the antioxidant include a phosphorous-included antioxidant, a phenolic antioxidant, a sulfur-included antioxidant, a combination comprising at least one of the foregoing, and the like.

Non-limiting examples of the plasticizer include polyethylene glycol, a polyamide oligomer, ethylene bis(stear) amide, ester phthalate, a polystyrene oligomer, liquid paraffin, polyethylene wax, silicone oil, a combination comprising at least one of the foregoing, and on the like.

Non-limiting examples of the flame retardant include brominatedpolystyrene, brominated syndiotactic polystyrene, brominated polyphenylene ether, brominated diphenylalkanes, brominated diphenyl ethers, a combination comprising at least one of the foregoing, and the like. In addition, the flame retardant may further include a further flame retardant of antimony trioxide.

The composition for forming a board may be prepared by blending the components in accordance with various methods, such as mixing at room temperature or fused-mixing the same.

The composition for forming a board including a liquid crystalline polymer or oligomer, a maleimide-based compound, and optionally other components is cast on a surface (for example, another board) to provide a thin film, and then is cured at elevated temperature. Prior to casting, the composition for forming a board may be filtered using a filter, and any impurities included in the solution may in this way be removed before the composition is coated or impregnated into, for example, a reinforcing material.

When the board is formed from the composition including a liquid crystalline polymer or oligomer and a maleimide-based compound including at least three maleimide groups, heat resistance may be improved and the board may not be brittle. In addition, since the liquid crystalline polymer or oligomer and the maleimide-based compound represented by Chemical Formulae 1 to 6 each have high solubility in the solvent, phase separation does not occur.

According to another embodiment, provided is a prepreg formed with the composition for forming a board. The prepreg may be fabricated by coating or impregnating a reinforcing material with the composition for forming a board, and drying the coated or impregnated reinforcing material to remove the solvent. Methods of impregnating include dip coating, roll coating, and the like. Non-limiting examples of the reinforcing material include woven glass fiber, woven alumina glass fiber, a non-woven glass fiber fabric, a non-woven cellulose fabric, woven carbon fiber, polymer fabrics, a combination comprising at least one of the foregoing, and the like. Exemplary reinforcing materials may include glass fiber, silica glass fiber, carbon fiber, alumina fiber, silicon carbide fiber, asbestos, rock wool, mineral wool, plaster, a woven or non-woven fabric thereof, aromatic polyamide fiber, polyimide fiber, liquid crystal polyester, polyester fiber, fluorinated fiber, polybenzoxazole fiber, glass fiber including polyamide fiber, glass fiber including carbon fiber, glass fiber including polyimide fiber, glass fiber including aromatic polyester, glass paper, mica paper, alumina paper, craft paper, cotton paper, paper-glass bond paper, a combination comprising at least one of the foregoing, and the like.

The prepreg may be bonded with a layer of copper, an alloy thereof, or other metal to form a laminate. For example, the composition for forming a board is coated on a copper foil or cast on a copper foil and heated to remove the solvent, so as to provide a member in which copper is bonded with the prepreg. In order to evaporate the solvent, the coated copper foil may be heated under a reduced pressure or may be ventilated. The coating may be performed by roller coating, dip coating, spray coating, spin coating, curtain coating, slit coating, screen printing, and like methods.

According to another embodiment, a board mounted with the prepreg is provided. For example, the board may be a flexible printed circuit ("FPC"). The board may be composed of a circuit metal layer and the prepreg. In this embodiment, a metal layer is deposited on the prepreg, and is laminated to the prepreg by pressing and heating in a presser to fuse and cure the prepreg. Exemplary metal layers may include copper, aluminum, iron, stainless steel, nickel, and the like, alloys thereof and the like, or a combination comprising at least one of the foregoing. In another embodiment a board may be formed in which both surfaces of the prepreg include metal layers. The board including the prepreg may include different structural features. For example, the board may be a single layer or may be multiple layers (e.g., two or more layers), where one or more metal layers may be patterned, unpatterned, or different surfaces may be patterned or unpatterned. For example, one surface or both surfaces of the board may be formed with a conductor pattern, and the conductor pattern may be formed in 4 layers or 8 layers of a multi-layer structure.

Hereinafter, the present invention is illustrated in more detail with reference to examples. However, they are exemplary embodiments of the present invention and should not be construed as limiting thereto.

SYNTHESIS EXAMPLE 1

Figure 4:
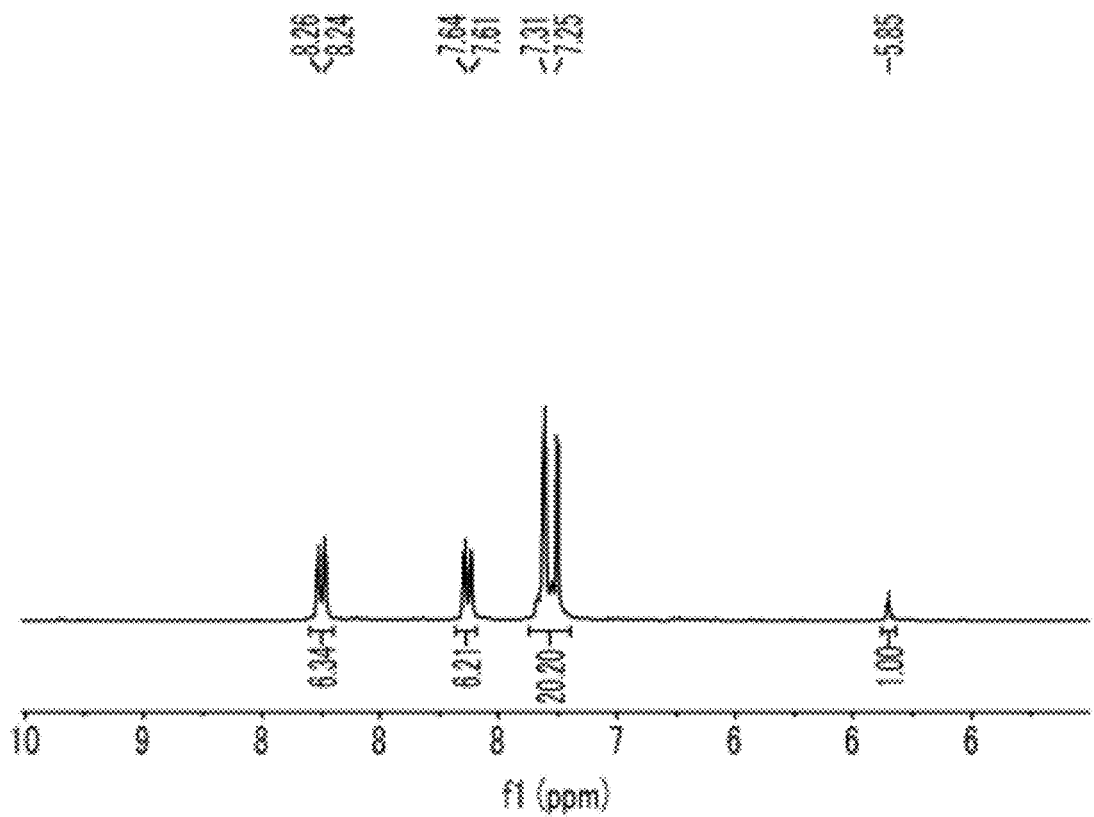
FIG. 4 is a $^1$H NMR spectrum of the exemplary compound according to Synthesis Example 1.

A maleimide-based compound is prepared by introducing 4.4 g of a compound represented by the following Chemical Formula 12 and 10.6 g of a compound represented by the following Chemical Formula 13 into 50 mL of a 1,2-dichloroethane solvent and reacting these in the presence of 3 mL triethylamine as an acid scavenger, for 2 hours. After removing triethylamine hydrochloride, 13.1 g of a compound represented by the following Chemical Formula 14 is obtained through filtration. A $^1$H NMR spectrum for the resultant compound represented by Chemical Formula 14 in DMSO-$d_6$ is shown in FIG. 4, and the data is as follows.

$^1$H NMR: 7.27-8.23 ppm (aromatic H), 7.24 ppm (—CH═), 5.84 ppm (CH).

Chemical Formula 15

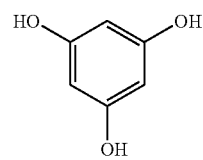

Chemical Formula 12

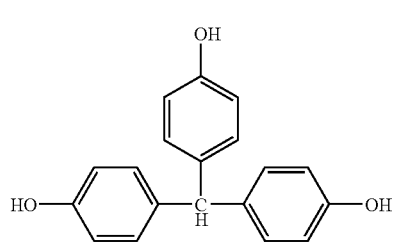

Chemical Formula 13

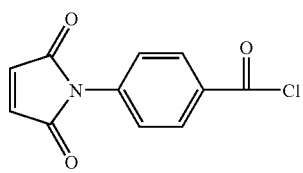

Chemical Formula 14

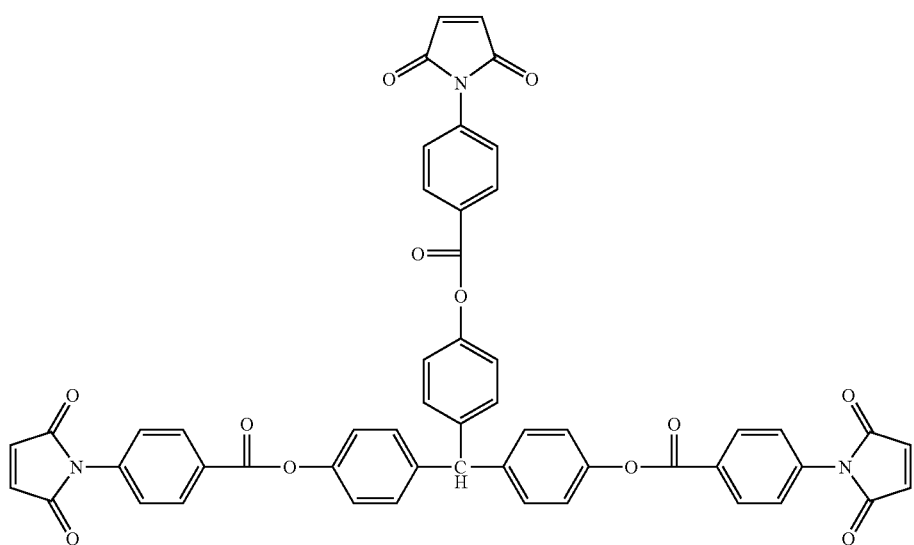

SYNTHESIS EXAMPLE 2

Figure 5:
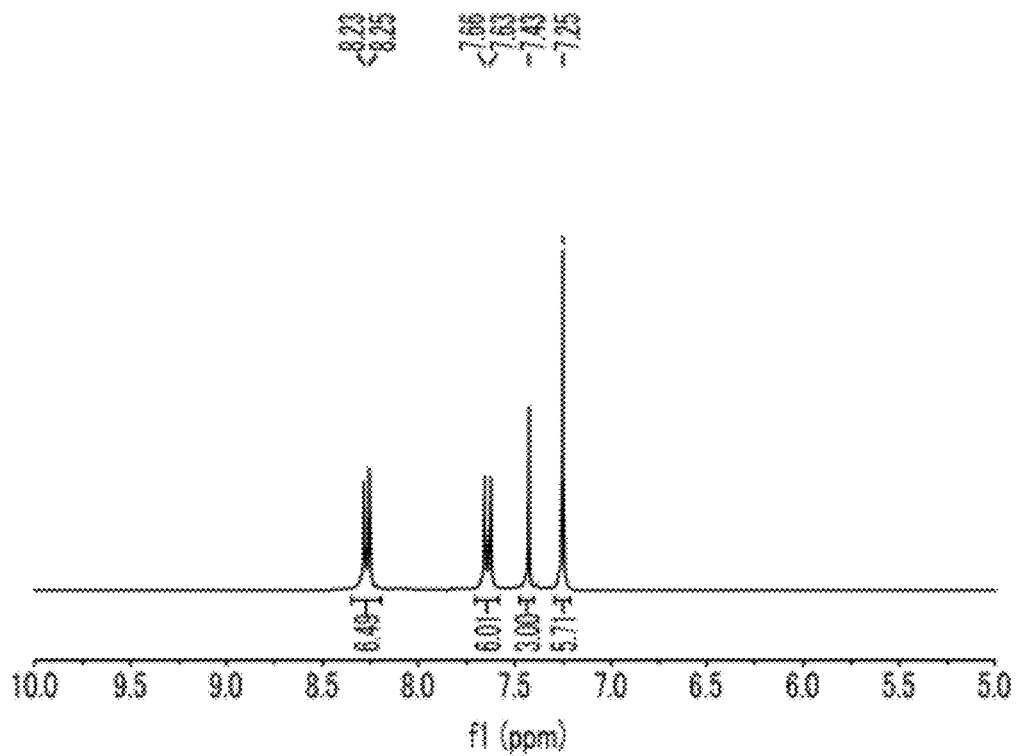
FIG. 5 is a $^1$H NMR spectrum of the exemplary compound according to synthesis example 2.

A maleimide-based compound represented by Chemical Formula 16 is prepared by the same procedure as in Synthesis Example 1, except that 1.26 g of a 1,3,5-trihydroxybenzene compound represented by Chemical Formula 15 and 7.4 g of a compound represented by Chemical Formula 13 are introduced into 40 mL of solvent, and 1 mL of triethylamine is used. After isolation, 4.8 g of a compound represented by the following Chemical Formula 16 is obtained. A $^1$H NMR spectrum for the compound represented by Chemical Formula 16 in DMSO-$d_6$ is shown in FIG. 5, and the data is as follows.

$^1$H NMR: 7.63-8.28 ppm (aromatic H from the maleimidobenzoate moiety, 12H), 7.43 (aromatic H from the phloroglucinol-derived moiety, 3H), 7.25 ppm (—CH═, 6H).

-continued

Chemical Formula 16

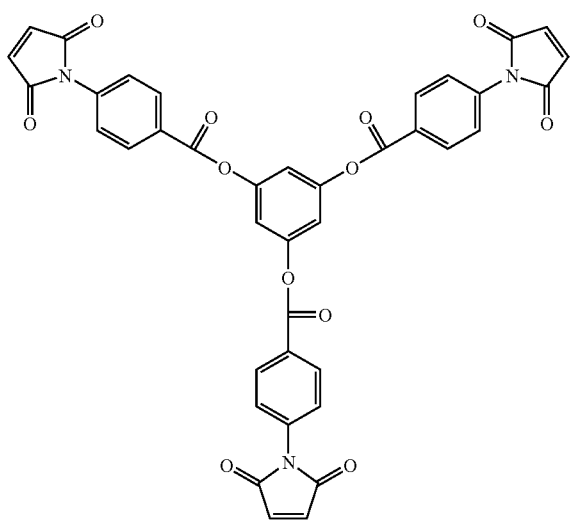

EXAMPLE 1

A composition is prepared from 0.6 g of a liquid crystalline oligomer represented by the following Chemical Formula 17 and 1.4 g of a maleimide-based compound represented by Chemical Formula 14 by introducing these into 3 mL of N-methyl-2-pyrrolidone (NMP) solvent. A glass fiber is impregnated with the obtained solution by dip coating. Subsequently, the glass fiber that is impregnated by the obtained solution is coated on a copper foil, and then it is cured in an electronic furnace at a high temperature of 300° C. for about one hour. The copper foil is removed with a nitric acid aqueous solution to provide the cured prepreg. The number of monomers participating in the polymerization reaction to form the cure product has a distribution according to the characteristics of melt polymerization in which the number averaged molecular weight of the polymerized product continually increases with increasing reaction time, and a and b of Chemical Formula 17 may each be integers from 1 to 50, respectively.

Chemical Formula 17

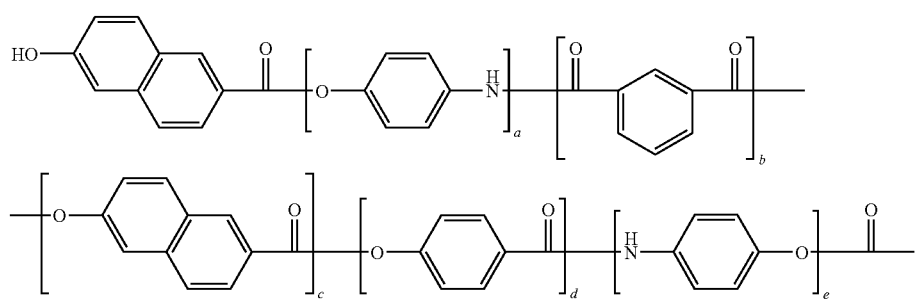

In the above Chemical Formula 17, a, b, c, d, and e are independently integers from 0 to 50, where $a+e \geq 1$, or $b+c+d \geq 1$. The number average molecular weight for Chemical Formula 17 is about 500 to about 10,000.

EXAMPLE 2

A composition is prepared in accordance with the same procedure as in Example 1, except that 1 g of a liquid crystalline oligomer represented by Chemical Formula 17 and 1 g of a maleimide-based compound represented by Chemical Formula 14 are used.

EXAMPLE 3

A composition is prepared in accordance with the same procedure as in Example 1, except that 1.4 g of a liquid crystalline oligomer represented by Chemical Formula 17 and 0.6 g of a maleimide-based compound represented by Chemical Formula 14 are used.

COMPARATIVE EXAMPLE 1

A composition is prepared in accordance with the same procedure as in Example 1, except that 0.6 g of a liquid crystalline oligomer represented by Chemical Formula 17 and 1.4 g of a maleimide-based compound represented by Chemical Formula 18 are used.

Chemical Formula 18

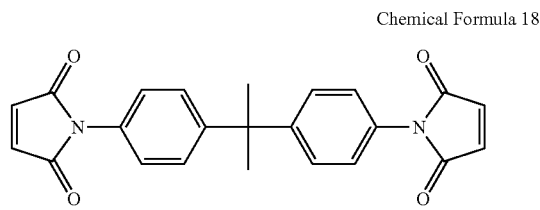

COMPARATIVE EXAMPLE 2

A composition is prepared in accordance with the same procedure as in Example 1, except that 1 g of a liquid crystalline oligomer represented by Chemical Formula 17 and 1 g of a maleimide-based compound represented by Chemical Formula 18 are used.

COMPARATIVE EXAMPLE 3

A composition is prepared in accordance with the same procedure as in Example 1, except that 1.4 g of a liquid crystalline oligomer represented by Chemical Formula 17 and 0.6 g of a maleimide-based compound represented by Chemical Formula 18 are used.

Measuring Thermal Expansion Coefficient

Each prepreg obtained from Examples 1 to 3 and Comparative Examples 1 to 3 is measured to determine the thermal expansion coefficient, expressed as parts per million per degree Kelvin (ppm/K) at temperatures from 50° C. to 150° C., and 50° C. to 300° C., by a thermo-mechanical analyzer, and the results are shown in the following Table 1. In Table 1, the weight ratio is the weight ratio of the liquid crystalline oligomer to the maleimide-based compound.

TABLE 1

|  | Weight ratio[a] | Impregnation Ratio (wt %) | Thermal expansion coefficient (ppm/K) | |
|---|---|---|---|---|
|  |  |  | 50-150° C. | 50-300° C. |
| Example 1 | 3:7 | 60 | 8.40 | 11.93 |
| Example 2 | 5:5 | 59 | 11.01 | 14.52 |
| Example 3 | 7:3 | 59 | 12.18 | 10.79 |
| Comparative Example 1 | 3:7 | 60 | 8.81 | 11.93 |
| Comparative Example 2 | 5:5 | 59 | 9.97 | 13.78 |
| Comparative Example 3 | 7:3 | 60 | 11.67 | 11.03 |

[a]Weight ratio of liquid crystal polymer/oligomer to maleimide-based compound.

As shown in Table 1, it can be seen in general that Examples 1 to 3 each have similar thermal expansion coefficients when compared to those of Comparative Examples 1 to 3.

Surface Characteristic

Figure 2:
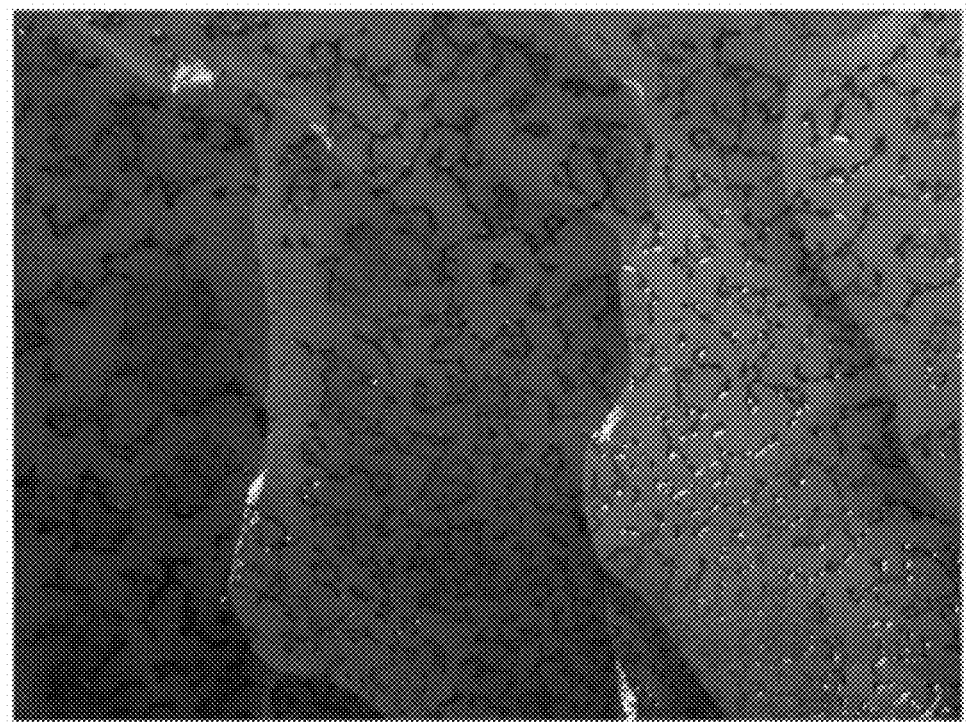
FIG. 2 is a SEM image showing the surface of a comparative prepreg according to Comparative Example 1.

A scanning electron micrograph (SEM) image of the prepregs obtained from Example 1 and Comparative Example 1 is taken to observe the surface characteristic, and the results are shown in FIG. 1 and FIG. 2, respectively.

FIG. 1 shows a homogeneous surface with no observable cracks, and shows no evidence the maleimide-based compound has phase-separated and deposited on the surface. In comparison, FIG. 2 shows numerous cracks generated at the surface, indicating brittleness in the cured comparative prepreg, and further shows deposition of the maleimide-based compound (dark patterns) on the prepreg surface.

Solubility Characteristic

Figure 3:
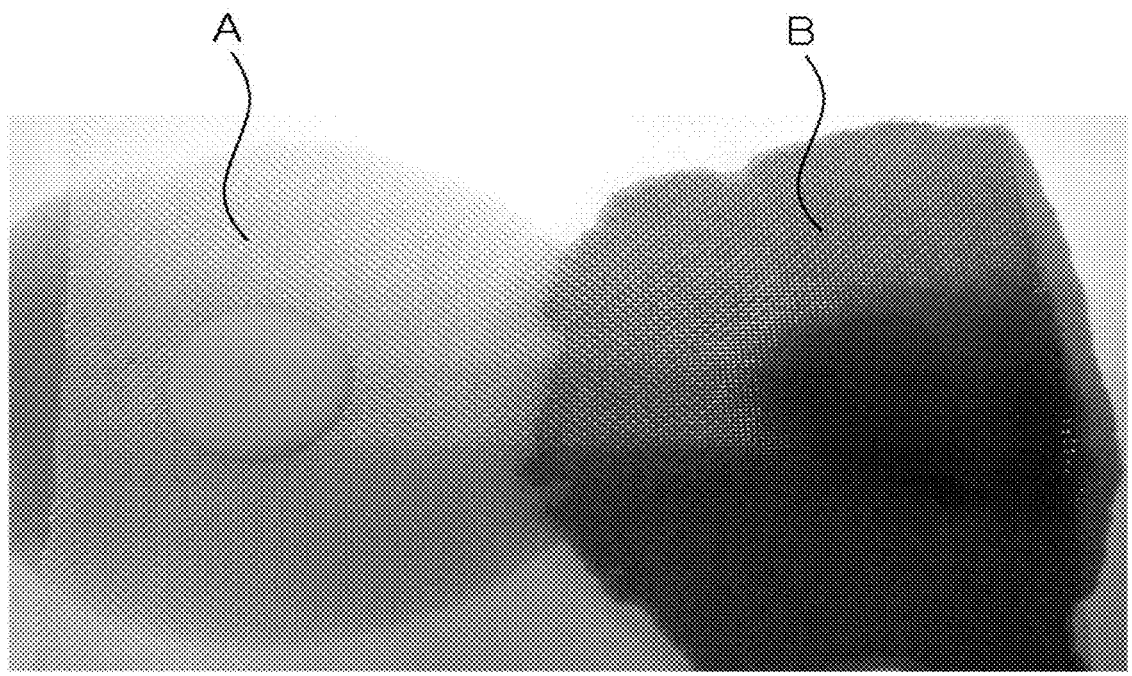
FIG. 3 is a SEM image showing an exemplary impregnated glass fiber according to Example 1 and a comparative impregnated glass fiber according to Comparative Example 1.

A woven glass fiber fabric is impregnated by each solution according to Example 1 and Comparative Example 1, and a SEM image of the glass fiber taken after two minutes, with results are shown in FIG. 3. FIG. 3 A shows the glass fiber impregnated with the solution of to Comparative Example 1; and FIG. 3B shows the glass fiber impregnated with the solution according to Example 1.

As shown in FIG. 3, it is confirmed that the glass fiber is impregnated with the solution of Example 1 at a higher speed relative to that of the Comparative Example 1.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A composition for forming a board, comprising:
   a monomeric maleimide-based compound including at least three maleimide groups, wherein the maleimide-based compound comprises a compound represented by the following Chemical Formula 1 or 2, or a combination thereof:

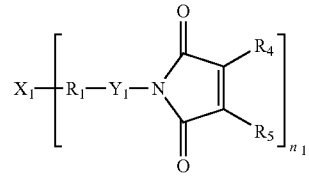

Chemical Formula 1

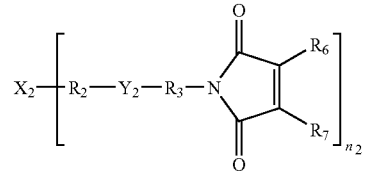

Chemical Formula 2 wherein, in the above Chemical Formulae 1 and 2,
$R_1$ to $R_3$ are independently a substituted or unsubstituted C6 to C24 arylene, $R_4$ and to $R_7$ are independently hydrogen or a C1 to C5 alkyl, $Y_1$ and $Y_2$ are independently C(=O)O, C(=O)NH, O, CO, or a combination thereof, and $n_1$ and $n_2$ are independently integers being from 3 to 5, provided that when $n_1$ is 3, $X_1$ is CR, P(=O), SiR, SiOR, or a combination thereof, where R is hydrogen or a C1 to C5 alkyl; when $n_1$ is 4, $X_1$ is C, Si, SiO, or a combination thereof; when $n_1$ is 5, $X_1$ is P, and when $n_2$ is 3, $X_2$ is CR, P(=O), SiR, SiOR, or a combination thereof, where R is hydrogen or a C1 to C5 alkyl; when n is 4, $X_2$ is C, Si, SiO, or a combination thereof; and when $n_2$ is 5, $X_2$ is P; and
a liquid crystalline polymer or liquid crystalline oligomer.

2. The composition for forming a board of claim 1, wherein the liquid crystalline polymer or oligomer comprises at least one of C(=O)O, O, C(=O)NR', NR', CO, a substituted or unsubstituted C6 to C30 aromatic cyclic group, or a combination thereof in its main chain, and where R' is hydrogen or a C1 to C5 alkyl.

3. The composition for forming a board of claim 2, wherein the liquid crystalline oligomer is represented by the following Chemical Formula 10-1:

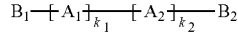

Chemical Formula 10-1 wherein, in the above Chemical Formula 10-1,
$A_1$ is represented by the following Chemical Formula 10-2, $A_2$ is represented by the following Chemical Formula 10-3, $B_1$ and $B_2$ are thermally curable cross-linking reactive end groups, each of which includes a double or triple bond at the terminus, and $k_1$ and $k_2$ are independently integers from 1 to 50,

Chemical Formula 10-2 wherein, in the above Chemical Formula 10-2,
$Y_3$ and $Y_4$ are independently C(=O)O, O, C(=O)NR, NR, CO, where R is hydrogen, a C1 to C20 alkyl, a C6 to C30 aryl, or a combination thereof, and $Ar_1$ is one selected from the group consisting of Chemical Formulae 7-1 to 7-5 and combinations thereof,

Chemical Formula 10-3 wherein, in the above Chemical Formula 10-3,
$Y_5$ and $Y_6$ are independently C(=O)O, O, C(=O)NR, NR, CO, or a combination thereof, where R is hydrogen, a C1 to C20 alkyl, a C6 to C30 aryl, or a combination thereof, and $Ar_2$ is one selected from the group consisting of the above Chemical Formulae 8-1 to 8-5 and combinations thereof,

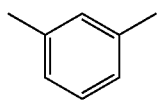
Chemical Formula 7-1

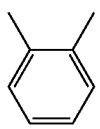
Chemical Formula 7-2

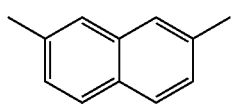
Chemical Formula 7-3

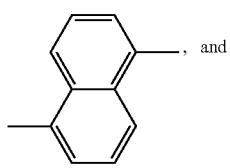, and
Chemical Formula 7-4

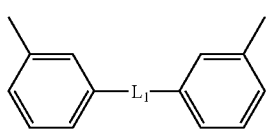
Chemical Formula 7-5 wherein, in the above Chemical Formula 7-5, $L_1$ is a divalent organic functional group,

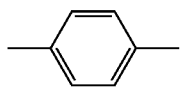
Chemical Formula 8-1

Chemical Formula 8-2

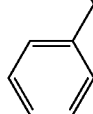
Chemical Formula 8-3

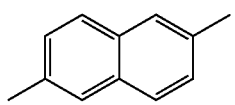, and
Chemical Formula 8-4

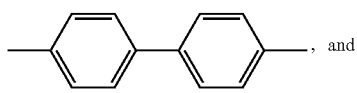
Chemical Formula 8-5 wherein, $L_2$ is a divalent organic functional group in the above Chemical Formula 8-5.

4. The composition for forming a board of claim 3, wherein, in the above Chemical Formula 10-1, the value $k_1/(k_1+k_2+2)$ is from about 0.5 to about 0.6.

5. The composition for forming a board of claim 3, wherein the liquid crystalline oligomer has a number average molecular weight of about 500 to about 10,000.

6. The composition for forming a board of claim 1, wherein the liquid crystalline polymer or oligomer comprises as an end group: a hydroxy; a maleimide group; a nadimide group; a phthalimide group; an acetylene group; a propargyl ether group; a benzocyclobutene; a cyanate; a substituted or unsubstituted alicyclic group which includes a double bond or a triple bond; an alkenyl including an aryl substituent; an alkynyl including an aryl substituent; or a combination thereof at its terminus.

7. The composition for forming a board of claim 6, wherein the liquid crystalline polymer or oligomer comprises a functional group selected from the group consisting of the following Chemical Formulae 11-1 to 11-6 and combinations thereof at the terminal end:

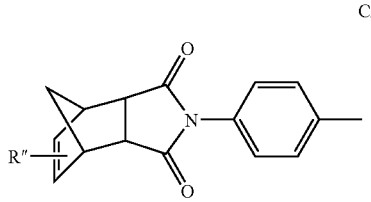
Chemical Formula 11-1

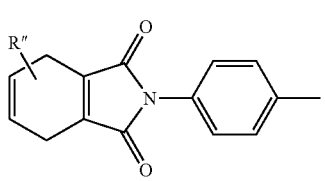
Chemical Formula 11-2

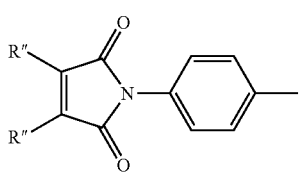
Chemical Formula 11-3

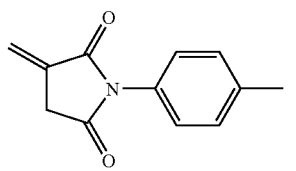
Chemical Formula 11-4

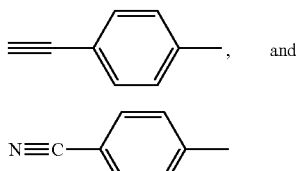, and
Chemical Formula 11-5

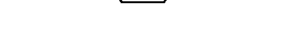
Chemical Formula 11-6 wherein, in the above Chemical Formulae 11-1 to 11-6, R″ is hydrogen, a substituted or unsubstituted C1 to C20 alkyl, a substituted or unsubstituted C6 to C30 aryl, or a combination thereof.

8. The composition for forming a board of claim 1, wherein the composition comprises the liquid crystalline polymer or oligomer and the maleimide-based compound respectively at a weight ratio of about 1:9 to about 9:1.

9. The composition for forming a board of claim 1, wherein the composition comprises an aprotic solvent.

* * * * *